US008066684B2

(12) United States Patent
Fujioka

(10) Patent No.: US 8,066,684 B2
(45) Date of Patent: Nov. 29, 2011

(54) DISPOSABLE PANTS

(75) Inventor: Masaru Fujioka, Tokushima (JP)

(73) Assignee: Livedo Corporation, Ehime (JP)

( * ) Notice: Subject to any disclaimer, the term of this patent is extended or adjusted under 35 U.S.C. 154(b) by 939 days.

(21) Appl. No.: 11/660,146

(22) PCT Filed: Aug. 12, 2005

(86) PCT No.: PCT/JP2005/014826
§ 371 (c)(1),
(2), (4) Date: Feb. 13, 2007

(87) PCT Pub. No.: WO2006/019049
PCT Pub. Date: Feb. 23, 2006

(65) Prior Publication Data
US 2007/0245447 A1 Oct. 25, 2007

(30) Foreign Application Priority Data

Aug. 17, 2004 (JP) ................................. 2004-237217

(51) Int. Cl.
*A61F 13/15* (2006.01)
*A61F 13/20* (2006.01)

(52) U.S. Cl. ......... 604/385.11; 604/385.29; 604/385.01; 604/387; 604/389; 604/391; 604/394

(58) Field of Classification Search ............. 604/385.11, 604/385.29, 385.04, 385.01
See application file for complete search history.

(56) References Cited

U.S. PATENT DOCUMENTS

| 6,508,799 B1 | 1/2003 | Freiburger et al. | |
|---|---|---|---|
| 6,579,275 B1 * | 6/2003 | Pozniak et al. | 604/390 |
| 6,605,071 B1 * | 8/2003 | Gray et al. | 604/385.28 |
| 7,077,834 B2 * | 7/2006 | Bishop et al. | 604/385.11 |
| 7,150,730 B2 * | 12/2006 | Hasler et al. | 604/385.11 |

(Continued)

FOREIGN PATENT DOCUMENTS

GB    2 267 024    11/1993

(Continued)

OTHER PUBLICATIONS

Supplemental European Search Report and Examiner's Opinion, issued Mar. 25, 2008 in European application 05 78 0230.8, which is a counterpart to the present application.

*Primary Examiner* — Leslie Deak
*Assistant Examiner* — Susan Su
(74) *Attorney, Agent, or Firm* — Wenderoth, Lind & Ponack, L.L.P.

(57) ABSTRACT

This invention provides disposable pants usable as both pants and a diaper, which ensure excellent stretchability to facilitate raising/lowering when putting them on, and the like. The disposable pants have functions of both pants and a diaper, and a left front abdominal part and a right front abdominal part can be expanded to the left and right by breaking left and right breaking parts. The left front abdominal part and right front abdominal part are provided with adhesive pieces attached/detached to/from an adhesive part of a central front abdominal part. The ratio between a lateral dimension of the front abdominal section in a stretched state and a lateral dimension between positions to which the left and right adhesive pieces are bonded, respectively, is set to fall within a range of $0.05 \leq X2/X1 \leq 0.55$, which ensures stretchability of the front abdominal section.

4 Claims, 7 Drawing Sheets

U.S. PATENT DOCUMENTS

| | | |
|---|---|---|
| 7,608,068 B2 * | 10/2009 | Fujioka .................... 604/385.11 |
| 2002/0148557 A1 * | 10/2002 | Heller et al. ................. 156/252 |
| 2003/0051805 A1 * | 3/2003 | Mlinar et al. ................ 156/269 |
| 2004/0182502 A1 * | 9/2004 | Wagner et al. ............... 156/204 |
| 2004/0186451 A1 * | 9/2004 | Bishop et al. ............ 604/385.11 |
| 2004/0225271 A1 * | 11/2004 | Datta et al. .............. 604/385.11 |
| 2005/0177125 A1 * | 8/2005 | Kondo .................... 604/385.29 |
| 2005/0192553 A1 * | 9/2005 | Hasler et al. ............. 604/385.11 |
| 2006/0135936 A1 * | 6/2006 | Markovich et al. ........... 604/386 |
| 2006/0259001 A1 * | 11/2006 | Roehrl et al. ............ 604/385.11 |
| 2008/0114322 A1 * | 5/2008 | Schmoker et al. ....... 604/385.03 |
| 2009/0198207 A1 * | 8/2009 | Torigoshi et al. ........ 604/385.29 |

FOREIGN PATENT DOCUMENTS

| | | |
|---|---|---|
| JP | 5-317356 | 12/1993 |
| JP | 2003-528649 | 9/2003 |
| JP | 2003-528650 | 9/2003 |
| WO | 96/08224 | 3/1996 |

* cited by examiner

DISPOSABLE PANTS

TECHNICAL FIELD

The present invention relates to disposable pants usable as both pants and as a diaper.

Today, disposable pants having stretchability around the hips, waist and legs so as to fit the wearer's body are in increasing demand. Such disposable pants are often used either for children or adults.

Such disposable pants are easy to raise/lower when putting them on and the like because of its aforementioned stretchability around the hips and the like, and are thus preferred particularly when taking care of bodily wastes for the elderly because the work of putting them on and taking them off is easy to perform.

However, such disposable pants, after having been soiled with bodily wastes, cause the inconvenience of having to take off garments put thereon in replacing them with new disposable pants.

Therefore, disposable pants usable as both pants and a diaper according to necessity have been presented. For instance, there are disposable pants disclosed in Japanese Patent Application Laid-Open No. 5-317356.

The disposable pants have breaking lines on both left and right sides of a front portion at which the front portion can be broken and have adhesive pieces bonded to left and right bonding parts of the front and rear portions. Then, when breaking the front portion at the breaking lines, the front portion and rear portion are fastened by the left and right adhesive pieces.

However, since the disposable pants disclosed in the aforementioned gazette are formed such that a strip of sheet to/from which the left and right adhesive pieces are attached/detached is provided almost across the entire width of the front portion, a problem arises in that the stretchability of the front portion cannot be taken advantage of and becomes insufficient, making it difficult to raise/lower them when putting them on, and the like.

DISCLOSURE OF INVENTION

To solve the aforementioned problems, the present invention has an object to provide disposable pants usable as both pants and a diaper, ensuring excellent stretchability, which facilitates raising/lowering when putting them on, and the like.

A first aspect of the present invention is disposable pants comprising a front abdominal section and a rear section having stretchability joined almost annularly and a crotch section provided to be joined between the front abdominal section and rear section, the crotch section being provided with an absorber, left and right breaking parts for breaking the front abdominal section being provided on both left and right sides of an area of the front abdominal section to which the crotch section is joined, wherein a first adhesive part is provided in at least part of a central area of the front abdominal section positioned between the left and right breaking parts on an exterior side, left and right adhesive pieces bonded to laterally outward sides of the left and right breaking parts in the front abdominal section are provided, second adhesive parts to be attached/detached to/from the first adhesive part are provided on the left and right adhesive pieces, respectively, and a ratio between a lateral dimension X1 of the front abdominal section in a stretched state and a lateral dimension X2 between positions to which the left and right adhesive pieces are bonded, respectively, is set to fall within a range of $0.05 \leq X2/X1 \leq 0.55$.

According to this aspect, the disposable pants have functions of both pants and a diaper, which are thus easy to raise/lower when putting them on, and the like.

Further, since the ratio between a lateral dimension X1 of the front abdominal section and a lateral dimension X2 between the positions to which the left and right adhesive pieces are bonded, respectively, is set to fall within a range of $0.05 \leq X2/X1 \leq 0.55$, an elastic area having stretchability can be sufficiently ensured in the front abdominal portion excluding an opening/closing area formed by the left and right adhesive pieces, wherein excellent stretchability around the hips can be ensured, which facilitates raising/lowering the disposable pants when putting them on, and the like.

Further, in a second aspect of the present invention, in the aforementioned first aspect, a ratio between the lateral dimension X1 of the front abdominal section in a stretched state and the lateral dimension X2 between positions to which the left and right adhesive pieces are bonded, respectively, is set to fall within a range of $0.10 \leq X2/X1 \leq 0.45$.

According to this aspect, since the ratio between the lateral dimension X1 of the front abdominal section and lateral dimension X2 between the positions to which the left and right adhesive pieces are bonded, respectively, fall within a range narrower than $0.10 \leq X2/X1 \leq 0.45$, the opening/closing area formed by the left and right adhesive pieces is not too small, efficiently preventing the opening/closing operation by the left and right adhesive pieces from becoming difficult, which ensures excellent workability.

Further, in a third aspect of the present invention, in the aforementioned first or second aspect, the left and right adhesive pieces are positioned within a lateral area of a front crotch part of the crotch section or bonded to almost the same positions as opposite sides of the lateral area, respectively.

According to this aspect, since the left and right adhesive pieces are positioned within a lateral area in a front crotch part of the crotch part or bonded to almost the same positions as opposite sides of the lateral area, respectively, the opening/closing operation by the left and right adhesive pieces can be performed in an area overlapping the front crotch part, which ensures excellent workability.

These and other objects, features, aspects and advantages of the present invention will become more apparent from the following detailed description of the present invention and accompanying drawings.

DETAILED DESCRIPTION OF THE INVENTION

First Embodiment

<General Description>

Figure 1:
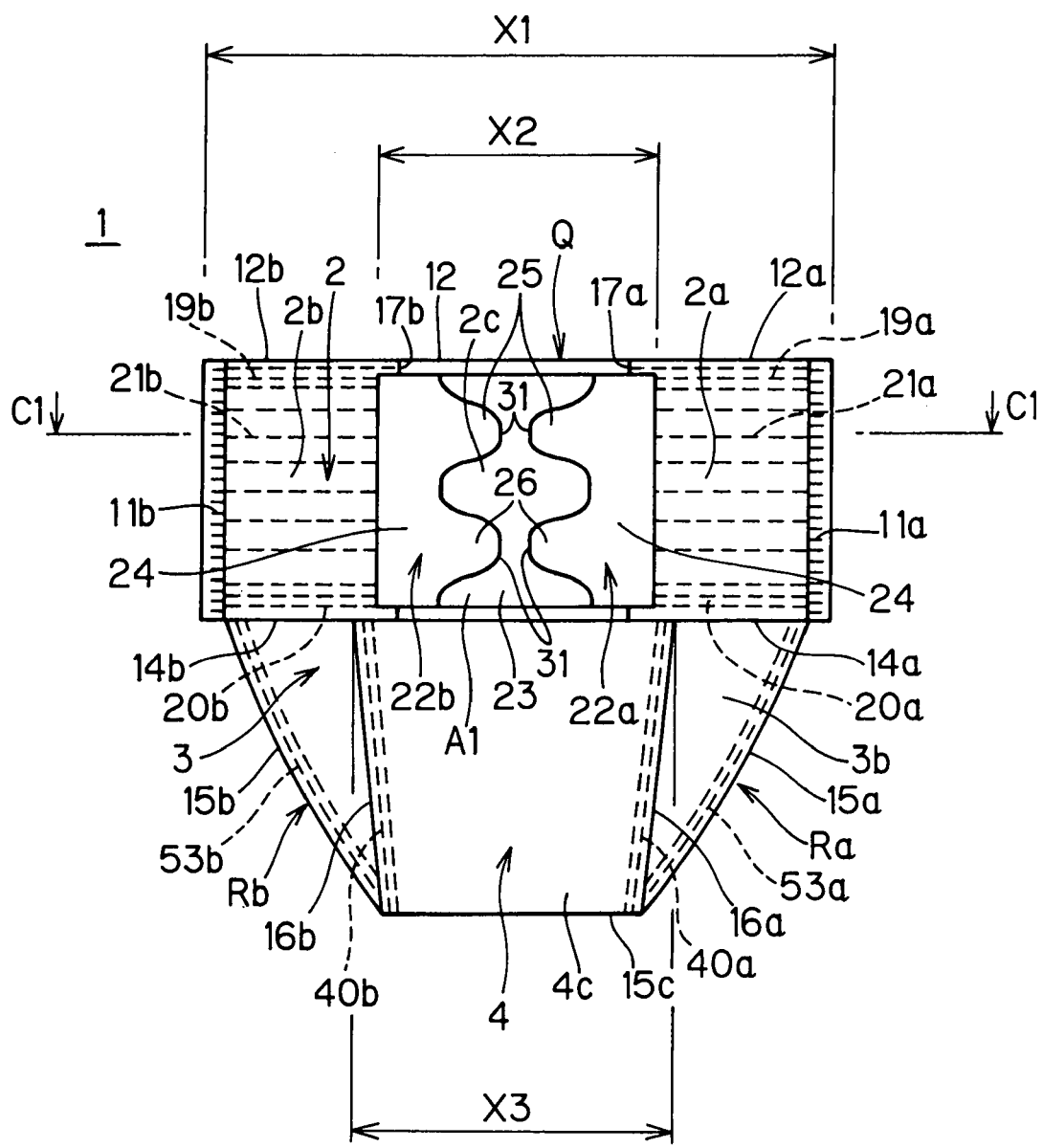
[FIG. 1] is a front view of disposable pants according to an embodiment of the present invention.

With reference to FIGS. 1 to 8, disposable pants 1 according to an embodiment of the present invention will be described. The disposable pants 1, as shown in FIGS. 1 to 8, are configured to comprise a front abdominal section 2 and a rear section 3 joined to each other almost annularly and a crotch section 4 provided to be joined between the front abdominal section 2 and rear section 3, and are usable as both pants and a diaper. In the description of the disposable pants 1, the left and right shall indicate the left hand side and right hand side as viewed from a wearer.

The front abdominal section 2 and rear section 3 refer to portions of the disposable pants 1 that mainly face a front abdominal area and an area on the back of a wearer. Left and right edges of the front abdominal section 2 and left and right edges of the rear section 3 are bonded to each other, and the front abdominal section 2 and rear section 3 are thereby joined almost annularly. Accordingly, a left side bonding part 11a and a right side bonding part 11b for bonding the left and right edges of the front abdominal section 2 and left and right edges of the rear section 3 are formed on left and right edges of the disposable pants 1. Bonding at these side bonding parts 11a and 11b is created either by bonding with an adhesive such as a hot melt adhesive or ultrasonic welding (or heating welding), or by both of them in combination.

The crotch section 4 indicates a portion of the disposable pants 1 that mainly faces the crotch of a wearer, having a front crotch part 4a and a rear crotch part 4b joined to the front abdominal section 2 and rear section 3, respectively. In this embodiment, the front crotch part 4a and rear crotch part 4b of the crotch section 4 are joined to the front abdominal section 2 and rear section 3 by an adhesive such as a hot melt adhesive. As a variant, the crotch section 4 may be formed integrally by a member connected to one or both of the front abdominal section 2 and rear section 3.

A waist opening Q is formed by upper edges 12 and 13 of such front abdominal section 2 and rear section 3 joined almost annularly. A left leg opening Ra is formed by a lower edge 14a of a left front abdominal part 2a of the front abdominal section 2, a sloped edge 15a on the left lower side of the rear section 3 and a left edge 16a of the crotch section 4. A right leg opening Rb is formed by a lower edge 14b of a right front abdominal part 2b of the front abdominal section 2, a sloped edge 15b on the right lower side of the rear section 3 and a right edge 16b of the crotch section 4.

<Front Abdominal Section>

Figure 2:
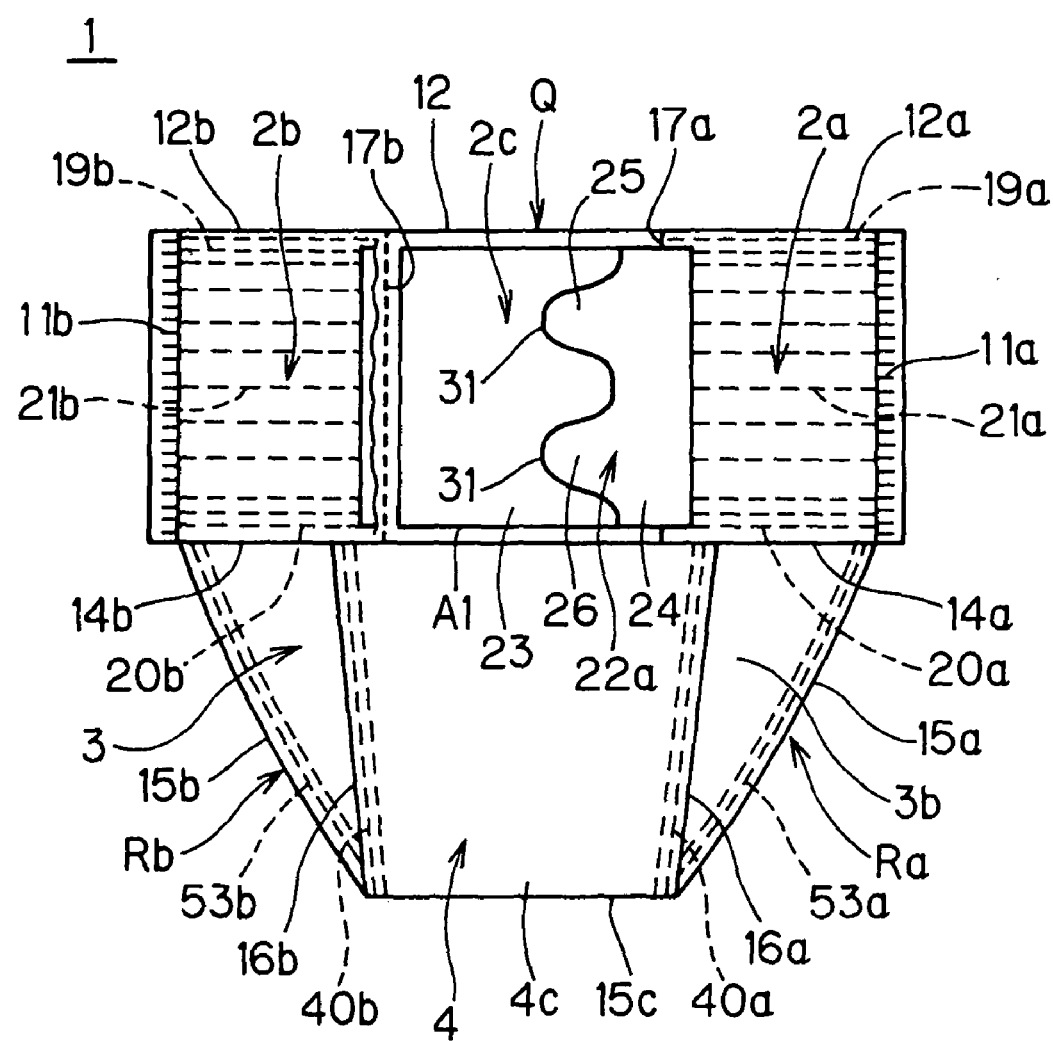
[FIG. 2] is a diagram in which a right adhesive piece of the disposable pants shown in FIG. 1 is broken.
Figure 6:
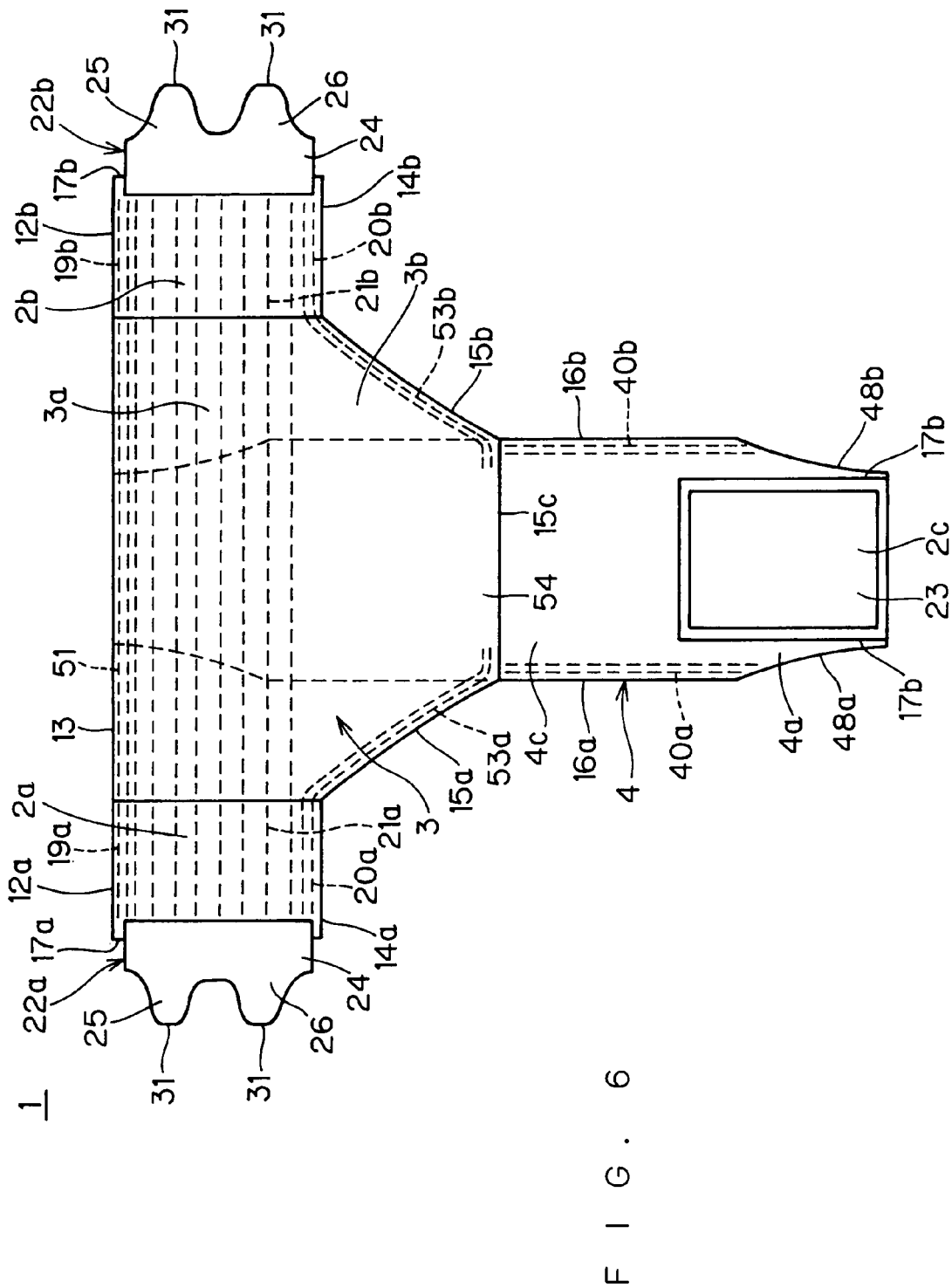
[FIG. 6] is a diagram of the disposable pants shown in FIG. 5 as viewed from the opposite side to FIG. 5.
Figure 7:
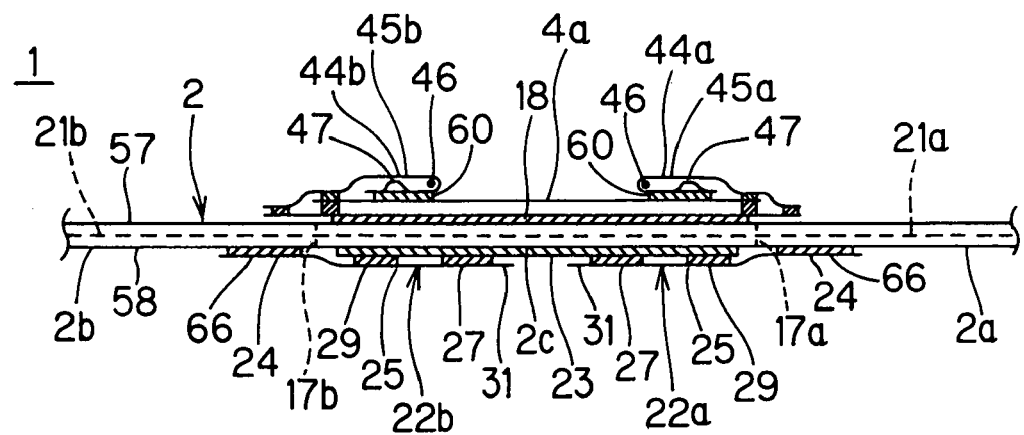
[FIG. 7] is a sectional view taken along a line C1-C1 of the disposable pants shown in FIG. 1.

The front abdominal section 2 is, as shown in FIG. 1, of almost laterally long rectangular shape in plan view as an overall configuration, and includes the left front abdominal part 2a, right front abdominal part 2b and a central front abdominal part 2c positioned midway between them. The central front abdominal part 2c corresponds to a central area of the present invention. A left breaking part 17a extending vertically through the front abdominal section 2 is formed between the left front abdominal part 2a and central front abdominal part 2c, and a right breaking part 17b extending vertically through the front abdominal section 2 is formed between the right front abdominal part 2b and central front abdominal part 2c. A bonding part 18 to the front crotch part 4a of the crotch section 4 is formed in the central front abdominal part 2c as shown in FIG. 7. Bonding at the bonding part 18 is created with an adhesive such as a hot melt adhesive. The breaking parts 17a and 17b are formed by perforations as shown in FIG. 2, and the front abdominal section 2 can be separated at the breaking parts 17a and 17b as shown in FIGS. 3 to 6 by breaking the breaking parts 17a and 17b. Here, the breaking parts 17a and 17b may be formed linearly as shown in FIG. 2 or may be formed in curved lines according to necessity.

Waist elastic members 19a and 19b are attached in a laterally stretched state to the upper edges 12a and 12b of the left front abdominal part 2a and right front abdominal part 2b. Leg elastic members 20a and 20b are attached in a laterally stretched state to the lower edges 14a, 14b of the left front abdominal part 2a and right front abdominal part 2b. Body elastic members 21a and 21b are attached in a laterally stretched state to areas of the left front abdominal part 2a and right front abdominal part 2b between the upper edges 12a and 12b and lower edges 14a and 14b of the left front abdominal part 2a and right front abdominal part 2b. Contraction and stretch of these elastic members 19a, 19b, 20a, 20b, 21a and 21b allows the front abdominal section 2 (particularly, left front abdominal part 2a and right front abdominal part 2b) to fit snugly about the abdominal area of a wearer.

Such front abdominal section 2 is formed by sandwiching the elastic members 19a, 19b, 20a, 20b, 21a and 21b between an interior-layer sheet 57 on the skin-facing side and an exterior-layer sheet 58 on the exterior side, as shown in FIG. 7.

Figure 4:
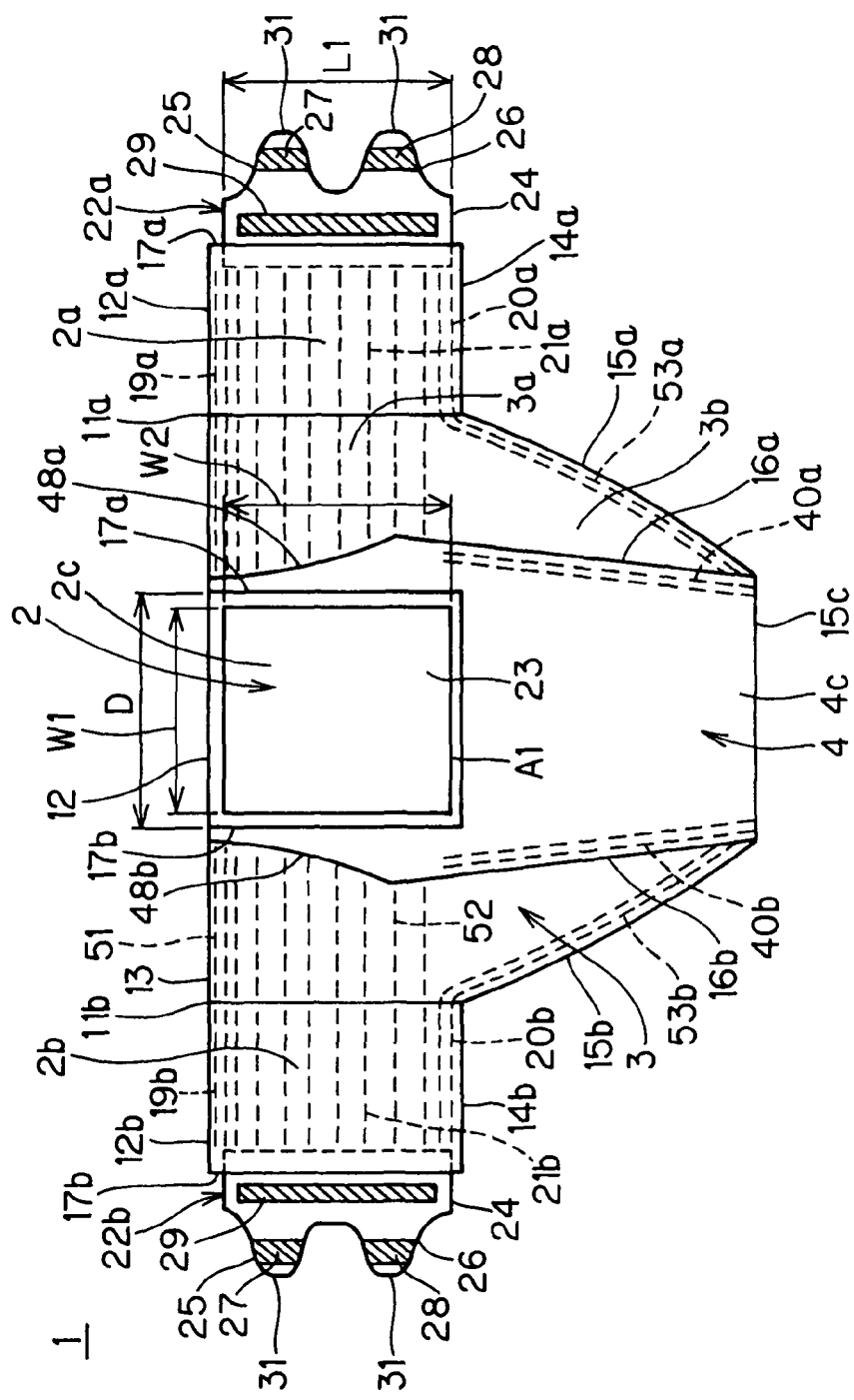
[FIG. 4] is a diagram showing the state in which a left breaking part of the disposable pants shown in FIG. 3 is broken to expand a left front abdominal part.

An almost sheet-like left adhesive piece 22a and a right adhesive piece 22b are bonded to the edges of the left front abdominal part 2a and right front abdominal part 2b on the exterior side and on the side of the central front abdominal part 2c with an adhesive such as a hot melt adhesive. These adhesive pieces 22a and 22b are used for securing the pants 1 when breaking the breaking parts 17a and 17b, and are provided to straddle the left and right breaking parts 17a and 17b on the exterior side of the front abdominal section 2. An adhesive part 23 corresponding to a first adhesive part to which the adhesive pieces 22a and 22b are to be attached is provided on the exterior side of the central front abdominal part 2c. This adhesive part 23 is formed continuously as a plane in a predetermined forming area A1. The lateral width W1 (widthwise dimension) of the forming area A1 is set at or smaller than the distance D between the left and right breaking parts 17a and 17b (i.e., widthwise dimension of central front abdominal part 2c) and the height W2 (lengthwise dimension) is set almost equal to the vertical dimension L1 (lengthwise dimension) of the adhesive pieces 22a and 22b, as shown in FIG. 4.

The adhesive pieces 22a and 22b each include an almost vertically long strip body 24 and two projections 25 and 26 bifurcated one on top of the other extending from the body 24 toward its free edge side. The body 24 has laterally outside edges bonded to the edges of the left front abdominal part 2a and right front abdominal part 2b on the side of the breaking parts 17a, 17b with an adhesive 66 such as a hot melt adhesive, as shown in FIG. 7.

The respective projections 25 and 26 of the adhesive pieces 22a and 22b are provided with adhesive parts 27 and 28, respectively, on the surface (interior side) facing the central front abdominal part 2c, and the body 24 is also provided with an adhesive part 29 on its interior side. These adhesive parts 27 to 29 correspond to second adhesive parts, and are attached to the adhesive part 23 provided on the central front abdominal part 2c freely detachably.

Specific examples of the adhesive part 23 may include a loop member having a nonwoven fabric, a woven fabric, a knitted material or the like with a fine loop structure being densely formed on its surface, and specific examples of the adhesive parts 27 to 29 may include a hook member with a fine hook structure in freely detachable engagement with the loop member being densely formed on its surface. More specifically, as the adhesive part 23, a plastic film composite material having on its surface a nonwoven fabric, a woven fabric or the like which is suitably used as a loop member for a hook-and-loop fastener is used for example. As the adhesive parts 27 to 29, a plastic film having pins densely formed on its surface which is suitably used as a hook member for a hook-and-loop fastener is used. Alternatively, a loop member may not be attached to the central front abdominal part 2c as a separate member, but the exterior surface of the central front abdominal part 2c may be surface-treated to serve as a loop member (adhesive part 23).

Alternatively, another specific example of the adhesive part 23 may include a plastic film or the like, which is surface-treated so as to have repetitive removability from an adhesive and the like, and another specific example of the adhesive parts 27 to 29 may include a reusable adhesive by using PEELOIL, for example.

In the above-described two specific examples of the aforementioned adhesive part 23 and those of the adhesive parts 27 to 29, the structure on the adhesive part 23 side and the structure on the adhesive parts 27 to 29 side may be replaced with each other.

Further, the tips of the respective projections 25 and 26 of the adhesive pieces 22a and 22b are tabs 31 (cf. FIG. 4) for easy lifting of the adhesive pieces 22a and 22b. These tabs 31 are not provided with adhesive parts 27 and 28.

Figure 3:
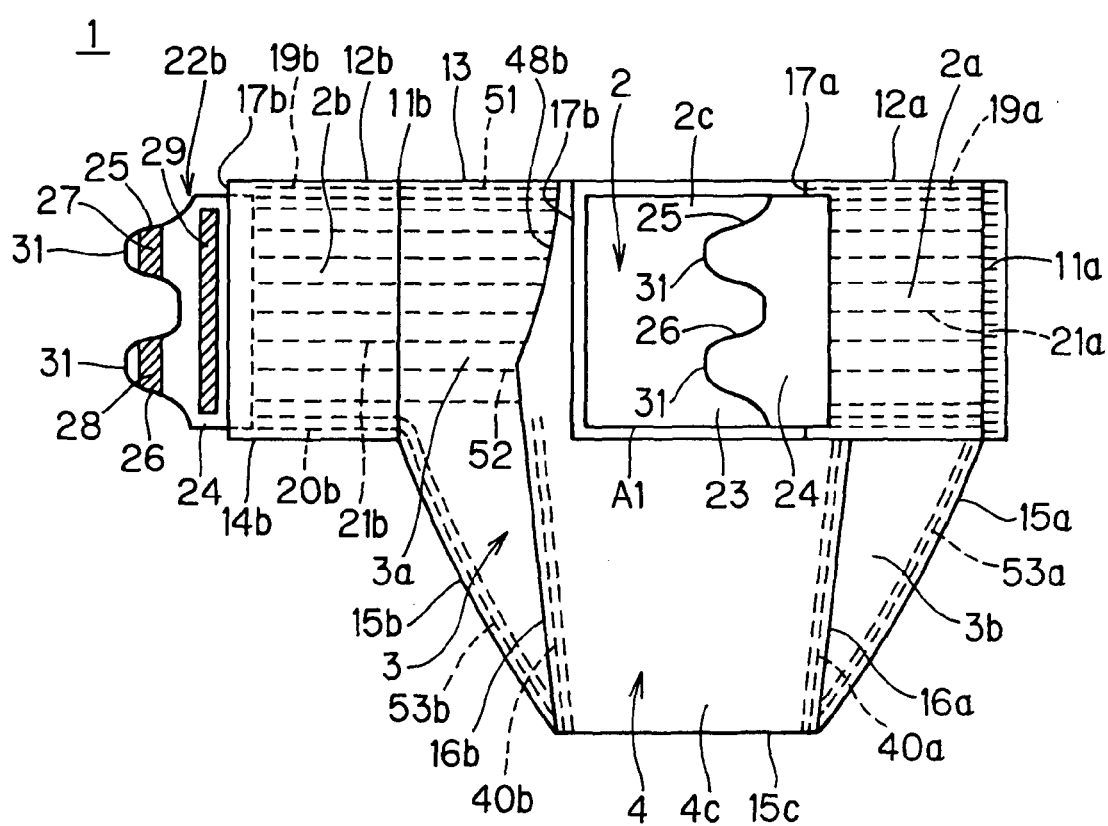
[FIG. 3] is a diagram showing the state in which a right breaking part of the disposable pants shown in FIG. 1 is broken to expand a right front abdominal part.

With such structure, when peeling the adhesive parts 27 to 29 of the right adhesive piece 22b from the adhesive part 23 while holding the projections 25 and 26 of the right adhesive piece 22b and pulling them outwardly to the right, the right breaking part 17b is broken as shown in FIG. 3, so that the right front abdominal part 2b is expanded to the right integrally with the right adhesive piece 22b. Similarly, when peeling the adhesive parts 27 to 29 of the left adhesive piece 22a from the adhesive part 23 while holding the projections 25 and 26 of the left adhesive piece 22a and pulling them outwardly to the left, the left breaking part 17a is broken as shown in FIG. 4, so that the left front abdominal part 2a is expanded to the left integrally with the left adhesive piece 22a. At this time, the central front abdominal part 2c is kept bonded to the crotch section 4 and remains on the exterior side of the front crotch part 4a.

Accordingly, the disposable pants 1, as shown in FIG. 7, function as pants since the front abdominal section 2 and crotch section 4 are secured by the bonding part 18 in the state at the time of shipping when the breaking lines 17a and 17b are yet to be broken, and are easily raised/lowered similarly to typical disposable pants having no opening/closing means such as the adhesive pieces 22a and 22b. Further, in this sate, the front abdominal section 2 and crotch section 4 are not separated from each other even if the engagement between the adhesive pieces 22a and 22b and adhesive part 23 is released.

Further, in the case where a wearer wears the disposable pants 1 as pants and when an absorber 43 to be described later absorbs and contains bodily wastes, the engagement of the adhesive pieces 22a and 22b may be released to break the breaking parts 17a and 17b, so that the pants 1 can easily be removed from the wearer. In this case, the pants 1 can be removed from the wearer without taking his/her garments off.

Further, after releasing the engagement of the adhesive pieces 22a and 22b to break the breaking parts 17a, 17b and expand the front abdominal section 2 to see how the inside of the pants 1 gets soiled, the adhesive pieces 22a and 22b may be engaged with the adhesive part 23, to thereby return the pants 1 to its original state as pants. Further, when the pants 1 and an optional pad such as a urine pad are used in combination, the adhesive pieces 22a and 22b can be attached/detached to facilitate replacing such optional pad, and the like.

Figure 5:
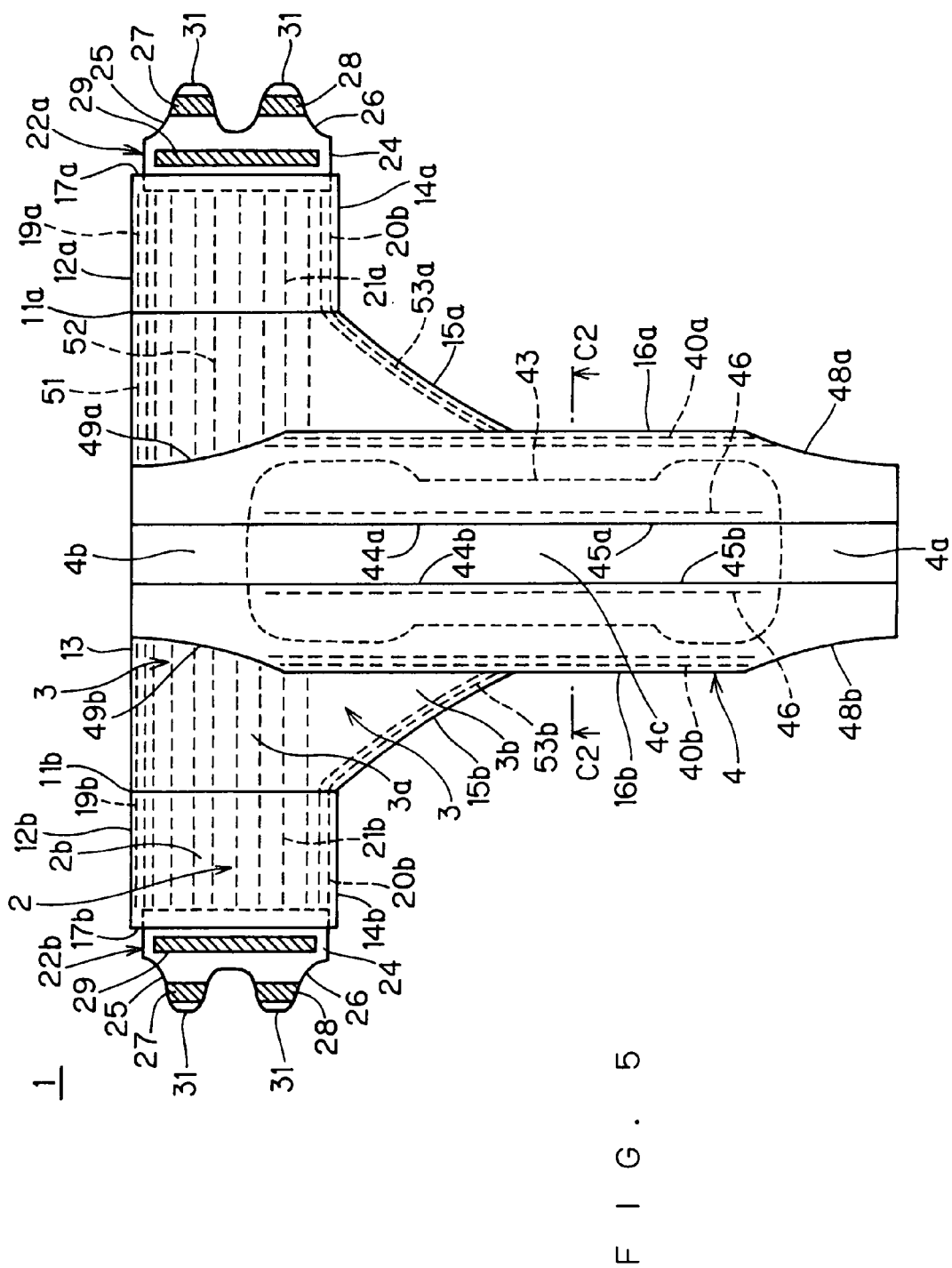
[FIG. 5] is a diagram showing the state in which a crotch section of the disposable pants shown in FIG. 4 is expanded.

Further, the pants 1 may be used as a typical disposable diaper applying the pants, as expanded as shown in FIG. 5 before putting them on, around the wearer's hips and then closing them as shown in FIGS. 4, 3 and 1 in this order, so that the pants 1 can be used as a typical disposable diaper. In this case, the pants 1 can be put on and removed without taking off wearer's garments.

Furthermore, in the present embodiment, as shown in FIG. 1, the ratio between the lateral dimension X1 of the front abdominal section 2 in a stretched state and lateral dimension X2 between the positions to which the left and right adhesive pieces 22a and 22b are bonded to the left and right front abdominal parts 2a and 2b, respectively, is set to fall within a range of $0.05 \leq X2/X1 \leq 0.55$. That is, when the disposable pants 1 are used for adults, the lateral dimension X1 of the front abdominal section 2 is typically about 450 mm to 900 mm, and most preferably, 500 mm to 720 mm. In this case, setting the relation between the lateral dimension X1 and lateral dimension X2 to fall within the above range ensures a relatively large width of the front abdominal section 2 excluding the opening/closing area formed by the left and right adhesive pieces 22a and 22b and the like, i.e., the left and right front abdominal parts 2a and 2b, which sufficiently ensures an elastic area having stretchability in the front abdominal section 2 as a whole, wherein excellent stretchability around the hips can be ensured, which facilitates raising/lowering the disposable pants when putting them on, and the like.

The width of the opening/closing area means the length between the outer edges of the left and right adhesive pieces 22a and 22b, which corresponds to the lateral dimension X2.

Accordingly, the opening/closing area is not too small, preventing the opening/closing operation by the left and right adhesive pieces 22a and 22b from becoming difficult, which ensures excellent workability.

More preferably, it is desirable that the ratio between the lateral dimension X1 of the front abdominal section 2 and lateral dimension X2 between the positions to which the left and right adhesive pieces 22a and 22b are bonded, respectively, fall within a range of $0.10 \leq X2/X1 \leq 0.45$. In this case, the opening/closing area is not too small so that a larger area is ensured, preventing with more efficiency the opening/closing operation by the left and right adhesive pieces 22a and 22b from becoming difficult, which ensures more excellent workability.

As a still more preferable aspect, it is desirable that the lateral dimension X2 satisfy $X2 \leq X3$ with respect to a lateral dimension X3 between the both edges of the front crotch part 4a of the crotch section 4. That is, it is formed such that the left and right adhesive pieces 22a and 22b are bonded, respectively, to positions within a lateral area of the front crotch part 4a or almost the same positions as the respective sides of the lateral area, which allows the opening/closing operation by the left and right adhesive pieces 22a and 22b to be performed in an area overlapping the front crotch part 4a. This facilitates the opening/closing operation, which ensures excellent workability.

<Crotch Section>

The crotch section 4, as shown in FIG. 5, has an almost strip shape extending in the front-to-rear direction when expanded as an overall configuration, including the front crotch part 4a, rear crotch part 4b and central crotch part 4c positioned midway between them, and is applied to the crotch of a wearer mainly setting the central crotch part 4c at the center. The front crotch part 4a, as shown in FIGS. 5 to 7, is bonded to the central front abdominal part 2c by the bonding part 18 while overlapping the interior side of the central front abdominal part 2c. The rear crotch part 4b, as shown in FIG. 5, is bonded and fixed to the rear section 3 while overlapping the interior side of the rear section 3. Leg elastic members 40a and 40b are attached to the left edge 16a and right edge 16b of such crotch section 4 in a stretched state in the direction that the edges 16a and 16b extend.

Figure 8:
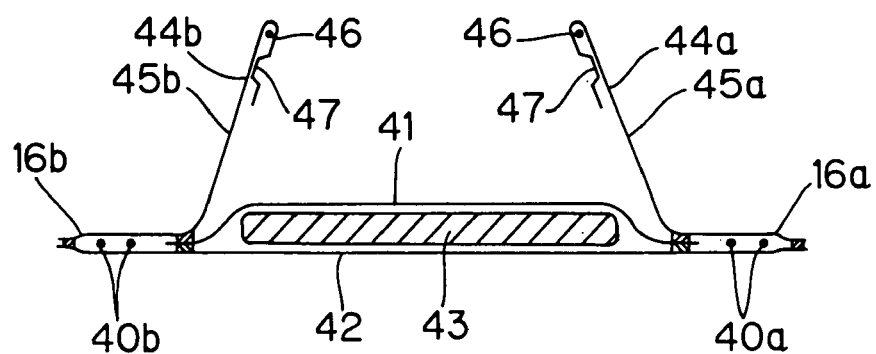
[FIG. 8] is a sectional view taken along a line C2-C2 of the disposable pants shown in FIG. 5.

The crotch section 4, as also shown in FIG. 8, is formed by sandwiching the absorber 43 between a liquid-permeable top sheet 41 and a liquid-impermeable backsheet 42. The absorber 43 has a predetermined width and extends in the front-to-rear direction in the form of strip with the central crotch part 4c set at the center. The both left and right sides of the absorber 43 on the interior side of the crotch section 4 are provided with standing parts 44a and 44b extending in the direction that the crotch section 4 extends.

For instance, the top sheet 41 is made of a liquid-permeable nonwoven fabric or the like, and the backsheet 42 is made of a water-repellant nonwoven fabric or the like. The absorber 43 is formed, for example, by covering a mass of a hydrophilic fiber assembly layer such as crushed pulp fibers or cellulose fibers mixed with a particulate gelling agent, with a covering sheet such as a sheet of paper like tissue paper, a liquid-permeable nonwoven sheet or the like, and is formed in a predetermined shape.

As to areas of the top sheet 41 and backsheet 42 that do not overlap the absorber 43, surfaces facing each other are bonded to each other with an adhesive such as a hot melt adhesive. More preferably, as shown in FIG. 8, the width of the top sheet 41 is determined to cover the skin-facing side of the absorber 43 and to be slightly narrower than the width of the backsheet 42, and portions of the top sheet 41 extending off the absorber 43 are bonded to the backsheet 42 with an adhesive such as a hot melt adhesive. Left and right side sheets 45a and 45b constituting the standing parts 44a and 44b are bonded to the skin-facing side of portions of the backsheet 42 extending off the top sheet 41 with an adhesive such as a hot melt adhesive.

Further, the both edges of the side sheets 45a and 45b in the front-to-rear direction are bonded to the both edges of the crotch section 4 in the front-to-rear direction with an adhesive 60 such as a hot melt adhesive. The laterally inside edges of the side sheets 45a and 45b are fixed by heating welding (or ultrasonic welding) or the like with sealing parts 47 so as to enclose elastic members 46 extending in the front-to-rear direction. The standing parts 44a and 44b have their laterally inside edges contracted by the contractive force of the elastic members 46, and are thereby raised in a direction to be pressed against the wearer's skin, as shown in FIG. 8.

Furthermore, in the present embodiment, as shown in FIG. 5, left and right edges of areas of the crotch section 4 that overlap the front abdominal section 2 and a waist zone 3a of the rear section 3 are sloped edges 48a, 48b, 49a and 49b, and have a gradually tapered width toward the edges in the front-to-rear direction.

These sloped edges 48a and 48b prevent the front abdominal part 2a from being hitched to curl up, become bent or affect the wearer's skin when raising/lowering the disposable pants 1, which allows smooth raising/lowering.

Further, while the contractive force of the rear section 3 generally tends to decrease in an area where the rear section 3 and crotch section 4 overlap, forming a trim area by the aforementioned sloped edges 49a and 49b gradually increases the area of the elastic part of the rear section 3 toward the top side of the rear section 3, which allows the rear section 3 to easily fit the wearer's back.

As an alternative structure of the crotch section 4, the absorber 43 may be adhered to the skin-facing side of the sheet 42, rather than sandwiching the absorber 43 between the sheets 41 and 42, and the sheet 41 may be omitted. Alternatively, the absorber 43 with sheets bonded to its front and rear edges may be used as the crotch section 4, or a large absorber 43 may be used as the crotch section 4 and the sheets 41 and 42 may be omitted.

<Rear Section>

The rear section 3, as shown in FIGS. 3 to 6, has such a form that, when expanded, left and right lower side corners of almost rectangle are cut almost diagonally, and is applied to an area from the waist to hips on the wearer's back. For this purpose, this rear section 3 includes the waist zone 3a in the form of almost laterally long strip in plan view mainly positioned on the waist on the wearer's back and a hip zone 3b of almost trapezoidal form in plan view joined downwardly to the waist zone 3a and mainly positioned on the wearer's hips. A waist elastic member 51 is attached in a laterally stretched state to the upper edge 13 of the waist zone 3a, and a body elastic member 52 is attached in a laterally stretched state to the other area of the waist zone 3a. A leg elastic member 53a is attached to the sloped edge 15a on the left lower side of the rear section 3 in a stretched state along the edge 15a, and a leg elastic member 53b is attached to the sloped edge 15b on the right lower side of the rear section 3 in a stretched position along the edge 15b. Contraction and stretch of these elastic members 51, 52, 53a and 53b allows the rear section 3 to easily fit the wearer's back and hips.

Particularly, the hip zone 3b of the rear section 3 is formed to have a gradually tapered width downwardly and the leg elastic members 53a and 53b provided on the left and right sloped edges 15a and 15b. Therefore, the hip zone 3b easily fits the wearer's hips when the edges 15a and 15b are contracted by the contractive forces of the leg elastic members 53a and 53b.

The leg elastic members 53a and 53b are continuously attached to the hip zone 3b along the left and right sloped edges 15a and 15b and lower edge 15c of the hip zone 3b, and then, at least an area 54 overlapping the absorber 43 of the crotch section 4 (cf. FIG. 6) is subjected to a weakening process. The weakening process is a process of cutting the elastic member in that area 54 or weakening its contractive force, or the like, to thereby bring about a no-tension state. This prevents the absorber 43 from causing an undesired contortion due to the contractive forces of the leg elastic members 53a and 53b and from degrading in its absorptive function.

<Other Structure and Material for Respective Parts, etc.>

As to the left and right elastic members 19a, 19b, elastic members 20a, 20b, and elastic members 21a, 21b provided in the front abdominal section 2, similarly to the case of the aforementioned leg elastic members 53a and 53b, it is preferable that the elastic members 20a, 20b, 21a and 21b be provided laterally continuously in the front abdominal section 2 through the central front abdominal part 2c, and then portions of the elastic members 20a, 20b, 21a and 21b positioned in the central front abdominal part 2c be subjected to the weakening process.

Further, the material for the adhesive pieces 22a and 22b may be selected appropriately from nonwoven fabrics, woven fabrics, knitted fabrics and plastic materials. Among them, a nonwoven fabric manufactured by one or a combination of a plurality of processes among spun-bond process, air-through process, point-bond process, melt-blow process and air-laid process is preferable. Further, a nonwoven fabric manufactured by a spun-bond process or SMS process combining the spun-bond process and melt-blow process with a weight of 30 to 100 g/m$^2$ is preferable in terms of strength. Most preferable is a nonwoven fabric manufactured by the spun-bond process with a weight of 50 to 85 g/m$^2$. The material can be selected appropriately from among synthetic fibers such as polypropylene, polyethylene, polyester, polyamide and the like and natural fibers such as pulp, silk and the like, but preferably, a synthetic fiber such as polypropylene, polyethylene or polyester can be used, and among them, one having a polypropylene or polyester fiber as its main component is strong and suitable. Most preferable one is a polyester fiber.

Further, for the elastic members 19a, 19b, 20a, 20b, 21a, 21b, 40a, 40b, 46, 53a and 53b, an elastic stretchable material (polyurethane thread, polyurethane film, natural rubber, etc.) typically used for disposable pants is employed, and is attached to a specified position of the pants 1 in a stretched state by adhering means such as a hot melt adhesive, heating welding, ultrasonic welding or the like.

As described above, the disposable pants 1 according to the present embodiment have functions of both pants and diaper, which are easy to raise/lower when putting them on, and the like.

Further, since the ratio between the lateral dimension X1 of the front abdominal section 2 and lateral dimension X2 between the left and right adhesive pieces 22a and 22b is set to fall within the range of $0.05 \leq X2/X1 \leq 0.55$, a relatively large width can be ensured for the front abdominal section 2 excluding the opening/closing area formed by the left and right adhesive pieces 22a and 22b and the like, i.e., the left and right front abdominal parts 2a and 2b, which sufficiently ensures an elastic area having stretchability in the front abdominal section 2 as a whole, wherein excellent stretchability around the hips can be ensured, which facilitates raising/lowering of the disposable pants when putting them on, and the like.

Further, since the lateral dimension X3 between the both edges of the front crotch part 4a of the crotch section 4 and the aforementioned lateral dimension X2 have a relation of $X2 \leq X3$, the opening/closing operation by the left and right adhesive pieces 22a and 22b can be performed in the area overlapping the front crotch part 4a, which facilitates the opening/closing operation and ensures excellent workability.

Further, since the left and right adhesive pieces 22a and 22b are provided with the two projections 25 and 26 bifurcated one on top of the other, securing the pants 1 making effective use of those two projections 25 and 26 allows fine adjustment of the shape of the pants 1 and fastening forces of respective parts in accordance with the wearer's body shape, which achieves improved fit about the wearer's body shape.

Further, since the adhesive part 23 is provided continuously nearly as a plane in the forming area A1 in the central front abdominal part 2c, the left and right adhesive pieces 22a and 22b can be attached to arbitrary positions in the forming area A1, which increases flexibility in the mode of securing.

Further, since the vertical width W2 of the forming area A1 forming the adhesive part 23 is set almost equal to the vertical dimension L1 of the left and right adhesive pieces 22a and 22b, the adhesive part 23 can be formed in necessary and sufficient range, which can reduce costs for forming the adhesive part 23.

The invention claimed is:

1. Disposable pants comprising:
   a front abdominal section and a rear section having stretchability, said front abdominal section and said rear section being joined almost annularly;
   a crotch section joined between the front abdominal section and rear section, said crotch section being provided with an absorber;
   left and right breaking parts provided on left and right sides, respectively, of an area of said front abdominal section to which said crotch section is joined, said left and right breaking parts being provided for breaking said front abdominal section into segments;
   a first adhesive part provided in at least part of a central area of said front abdominal section positioned between said left and right breaking parts on an exterior side;
   a left adhesive piece bonded to said front abdominal section on an opposite side of said left breaking part relative to said first adhesive part, said left adhesive piece being releasably attachable to said first adhesive part; and
   a right adhesive piece bonded to said front abdominal section on an opposite side of said right breaking part relative to said first adhesive part, said right adhesive piece being releasably attachable to said first adhesive part;
   wherein a distance X2 is provided between a position at which said left adhesive piece is bonded to said front abdominal section on said opposite side of said left breaking part relative to said first adhesive part and a position at which said right adhesive piece is bonded to said front abdominal section on said opposite side of said right breaking part relative to said first adhesive part;
   wherein second adhesive parts to be attached/detached to/from said first adhesive part are provided on said left and right adhesive pieces, respectively, and
   wherein said disposable pants are configured such that a ratio of a lateral dimension X1 of said front abdominal section in a stretched state to said distance X2 is within a range of $0.05 \leq X2/X1 \leq 0.55$.

2. The disposable pants according to claim 1, wherein a ratio of the lateral dimension X1 to the lateral dimension X2 is within a range of $0.10 \leq X2/X1 \leq 0.45$.

3. The disposable pants according to claim 1, wherein said left and right adhesive pieces are positioned within a lateral area of a front crotch part of said crotch section or bonded to substantially the same positions as opposite sides of the lateral area, respectively.

4. The disposable pants according to claim 2, wherein said left and right adhesive pieces are positioned within a lateral area of a front crotch part of said crotch section or bonded to substantially the same positions as opposite sides of the lateral area, respectively.

* * * * *